United States Patent [19]

Hamprecht et al.

[11] Patent Number: 4,514,572
[45] Date of Patent: Apr. 30, 1985

[54] PREPARATION OF FLUOROPHTHALIC ANHYDRIDES

[75] Inventors: Gerhard Hamprecht, Weinheim; Juergen Varwig, Heidelberg; Wolfgang Rohr, Wachenheim, all of Fed. Rep. of Germany

[73] Assignee: BASF Aktiengesellschaft, Ludwigshafen, Fed. Rep. of Germany

[21] Appl. No.: 572,949

[22] Filed: Jan. 23, 1984

[30] Foreign Application Priority Data

Feb. 2, 1983 [DE] Fed. Rep. of Germany ...... 3303378

[51] Int. Cl.³ .......................................... C07D 307/89
[52] U.S. Cl. .................................................. 549/246
[58] Field of Search ....................................... 549/246

[56] References Cited

U.S. PATENT DOCUMENTS 2,891,074 6/1959 Scherer et al. ...................... 260/384

FOREIGN PATENT DOCUMENTS 55630 7/1982 European Pat. Off. .

OTHER PUBLICATIONS

Heller, J. Org. Chem. 25, (1960), p. 834.

Primary Examiner—Richard L. Raymond
Attorney, Agent, or Firm—John H. Shurtleff

[57] ABSTRACT

Fluorophthalic anhydrides containing 1 or 2 fluorine atoms are prepared by a process in which a chlorophthalic anhydride containing 1 or 2 chlorine atoms is treated with an acid chloride of sulfurous acid or of carbonic acid in the presence of an aliphatic sulfone, and the reaction mixture is then reacted with potassium fluoride.

2 Claims, No Drawings

PREPARATION OF FLUOROPHTHALIC ANHYDRIDES

The present invention relates to a novel process for the preparation of fluorophthalic anhydrides by treatment of the corresponding chlorophthalic anhydride with an acid chloride of sulfurous acid or of carbonic acid in the presence of an aliphatic sulfone, followed by reaction with potassium fluoride.

J. Org. Chem. 25, (1960), 834 discloses that 3-fluorophthalic anhydride can be prepared by heating 3-chlorophthalic anhydride with excess potassium fluoride. In this process, 3-fluorophthalic anhydride is obtained in a yield of 50%. The same process is also described in EP-A-55,630, where it is stated that heating at 235° C. for several hours gives a reaction mixture from which a 3-fluorophthalic anhydride is obtained in a yield of 68% by distillation and recrystallization, the purity of the product not being specified. In the corresponding preparation of 4,5-difluorophthalic anhydride, the yield is only 66%. According to EP-A-55,630, page 4, lines 29–33, this reaction can also be carried out in the presence of a dipolar aprotic solvent, eg. sulfolane, but the solvent-free mixture is preferred.

According to Example 8 of U.S. Pat. No. 2,891,074, heating 4-chlorophthalic anhydride with a large excess of potassium fluoride in an autoclave for 24 hours at 200° C. gives 4-fluorophthalic anhydride in a yield of 52%.

We have found that fluorophthalic anhydrides of the formula:

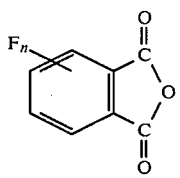

where n is 1 or 2, can be prepared much more advantageously, by reacting a chlorophthalic anhydride of the formula

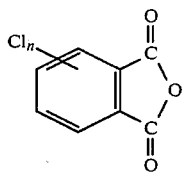

where n has the above meanings, with potassium fluoride in the presence of an aliphatic sulfone as a solvent, if the chlorophthalic anhydride is treated with an acid chloride of sulfurous acid or carbonic acid in the presence of the aliphatic sulfone at as high as 150° C., and the reaction mixture is then reacted with potassium fluoride at from 150° to 250° C.

Compared with the conventional processes, the process according to the invention gives a considerably improved result in respect of the yield and the purity of the fluorophthalic anhydrides. This is also substantially superior to the conventional preparation processes in that shorter reaction times and a smaller amount of potassium fluoride are required.

In the novel process, a chlorophthalic anhydride of the formula II, eg. 3-chlorophthalic anhydride, 4-chlorophthalic anhydride, 3,6-dichlorophthalic anhydride, 4,5-dichlorophthalic anhydride, 3,5-dichlorophthalic anhydride or 3,4-dichlorophthalic anhydride, is treated in a first stage with an acid chloride of sulfurous acid or of carbonic acid, eg. thionyl chloride or phosgene, in the presence of an aliphatic sulfone at as high as 150° C.

Examples of suitable aliphatic sulfones are the compounds of the formula

where $R^1$ and $R^2$ are identical or different and are each an aliphatic radical, preferably alkyl of 1 to 8, in particular 1 to 4, carbon atoms, or $R^1$ and $R^2$ together form an alkylene radical of 4 or 5 carbon atoms. Examples of suitable solvents of the stated type are dimethyl sulfone, diethyl sulfone, dipropyl sulfone, diisopropyl sulfone, dibutyl sulfone, diisobutyl sulfone, methyl ethyl sulfone, tetramethylene sulfone (sulfolane) and pentamethylene sulfone, sulfolane being preferred. Advantageously, the solvent is used in an amount of from 50 to 1,000, preferably from 100 to 300, % by weight, based on starting material II. The acid chloride is advantageously employed in an amount of from 1 to 20, preferably from 2 to 12, % by weight, based on the sulfone III.

The first stage of the process is carried out at as high as 150° C., advantageously at from 50° to 120° C., in particular at from 70° to 100° C. The starting material II, the sulfone III and the acid chloride can be mixed with one another in any sequence in the stated temperature range. Advantageously, however, the starting material II is first mixed with the sulfone III and, if required, a catalyst at from 30° to 40° C., the acid chloride is then added to the stirred mixture, and the resulting mixture is heated to a temperature within the stated range. Heating is advantageously continued until evolution of gas is no longer observed. It is preferable to remove excess acid chloride, for example by blowing in an inert gas, eg. nitrogen, or by reducing the pressure.

Examples of suitable catalysts for this process stage are N,N-disubstituted carboxamides of 3 to 10 carbon atoms, eg. N,N-dimethylformamide, N,N-dimethylacetamide, N,N-diethylformamide, N,N-di-n-propylacetamide, N-methyl-N-ethylformamide and N,N-diisopropylacetamide. The catalyst is advantageously used in an amount of from 0.2 to 2% by weight, based on the acid chloride.

The reaction mixture from the first stage of the process is reacted in a second stage with potassium fluoride at from 150° to 250° C., in particular from 170° to 240° C., preferably from 190° to 220° C., under atmospheric or superatmospheric pressure, using a continuous or batchwise procedure. The potassium fluoride is used in an amount of, for example, from 1 to 1.4, preferably from 1.1 to 1.2, moles per gram equivalent of chlorine in the starting material II. The procedure is carried out, for example, as follows: the potassium fluoride which advantageously is dried beforehand, is added to the mixture obtained from the first process stage, and the mixture obtained by stirring is kept at the reaction temperature for from 1 to 10 hours.

The halogen exchange proceeds at a high velocity even in the absence of a catalyst, but can be accelerated by adding a crown ether or a cryptand. These are organic ligands which are particularly useful for binding alkali. Crown ethers are neutral cyclic ethylene glycol ethers. The cryptands form a three-dimensional cage. Regarding the preparation of these substances, reference may be made to Kontakte (1977), pages 11–31 and 36–48. Preferred catalysts for the second stage of the novel process are crown ethers, the following compounds being suitable examples of these: 12-crown-4, 2,4,6,8-tetramethyl-12-crown-4, 14-crown-4, dibenzo-14-crown-4, dibutylbenzo-14-crown-4, dicyclohexyl-14-crown-4, 15-crown-5, 1,2-benzo-15-crown-5, 1,2-butylbenzo-15-crown-5, 1,2-cyclohexyl-15-crown-5, dibenzo-15-crown-5, 16-crown-5, dibenzo-16-crown-5, 18-crown-5, dibenzo-18-crown-5, 18-crown-6, benzo-18-crown-6, cyclohexyl-18-crown-6, dibenzo-18-crown-6, dicyclohexyl-18-crown-6, tribenzo-18-crown-6, dinaphtho-18-crown-6, 19-crown-6, dibenzo-19-crown-6, 20-crown-7, dibenzo-5-hydroxy-20-crown-7, 21-crown-7, dibenzo-21-crown-7, dicyclohexyl-21-crown-7, 24-crown-8, dibenzo-24-crown-8, dicyclohexyl-24-crown-8, tetrabenzo-24-crown-8, 30-crown-10, 40-crown-20, aza-18-crown-6, dibenzoaza-18-crown-6, diaza-18-crown-6, dibenzodiaza-18-crown-6, 1,4-dithia-15-crown-5, 1,4-dithia-18-crown-6, 1,7-dithiabenzo-18-crown-6, 1,10-dithiabenzo-18-crown-6 and 1,7,10,16-tetrathia-18-crown-6.

The catalyst is advantageously used in an amount of from 0.05 to 0.5, in particular from 0.1 to 0.3, mole percent per mole of starting material II.

After the reaction with potassium fluoride, which is complete after about ½–8 hours, working up is carried out in a conventional manner, for example by filtration, washing of the solid, and distillation of the filtrate and washings. Since the fluorophthalic anhydrides obtainable by the novel process distil within a range similar to that for sulfolane, any residual end product I can be extracted azeotropically by adding a little sulfolane to the distillation residue, and can be filtered off under suction after the distillate has been cooled.

The fluorophthalic anhydrides thus obtained are useful starting materials for the preparation of dyes, drugs and crop protection agents.

In the Examples which follow, parts are by weight.

EXAMPLE 1

96 parts of thionyl chloride are added to a stirred mixture of 500 parts of 3-chlorophthalic anhydride and 800 parts of sulfolane at 40° C., and the reaction mixture is heated to 100° C. in the course of 20 minutes and stirred at this temperature for 30 minutes until the evolution of gas is complete. Excess thionyl chloride is then stripped off in the course of 10 minutes under reduced pressure from a water pump, the temperature decreasing to 90° C. 190.9 parts of potassium fluoride are then introduced into the reaction solution at the same temperature, and the mixture is stirred for 3 hours at 205° C. By means of gas chromatography carried out on a sample, it is possible to show that, in addition to sulfolane, pure 3-fluorophthalic anhydride is present, complete conversion having taken place. Within the detection limit, 3-chlorophthalic anhydride is not detectable.

The reaction mixture is cooled to 40° C. and filtered under suction, and the residue is washed with 100 parts of acetone. The filtrate is freed from acetone in a rotary evaporator at 50° C./10 mbar, and is then introduced via a dropping funnel, at 200° C./0.3 mbar, into a distillation apparatus having a capacity of 500 parts by volume, so that sulfolane distils over continuously together with 3-fluorophthalic anhydride. Finally, for the extractive distillation of remaining amounts of end product in the residue, a further 126 g of sulfolane are introduced into the distillation apparatus through the dropping funnel. A total of 1,317.4 parts of distillate is obtained. The sulfolane (926 parts) is stripped off to give 391.4 parts (yield 86.1% of theory) of 3-fluorophthalic anhydride. About one third of the amount of this product crystallizes when the distillate is cooled. The crystals are filtered off under suction and washed with toluene and pentane to give 117 parts of 3-fluorophthalic anhydride of melting point 158°–160° C. The remainder stays dissolved in the filtrate. According to a gas chromatographic investigation using a 2 m SE 30 column (Chromosorb W, 80–100 mesh, coated with 20% of SE 30 silicone rubber) at 220° C., the residue and the filtrate contain the identical pure 3-fluorophthalic anhydride.

EXAMPLE 2

35 parts of thionyl chloride are added to a stirred mixture of 240 parts of 3-chlorophthalic anhydride and 504 parts of sulfolane at 36° C., and the reaction mixture is heated to 110° C. in the course of 15 minutes and then stirred at this temperature for a further 25 minutes until the evolution of gas is complete. Excess thionyl chloride is then stripped off in the course of 10 minutes under reduced pressure from a water pump.

84 parts of potassium fluoride and 0.7 part of 18-crown-6 are then added to the mixture at 90° C., and stirring is continued for 2 hours at 210° C. The mixture is cooled, and is worked up as described in Example 1. Subsequent azeotropic distillation with 126 parts of sulfolane gives a total of 820 parts of distillate. It contains 190 parts (87% of theory) of 3-fluorophthalic anhydride. A sample filtered off under suction and washed with toluene and pentane has a melting point of 158°–160° C. Gas chromatographic investigation shows that the filtrate contains, apart from sulfolane, only pure 3-fluorophthalic anhydride.

EXAMPLE 3

16 parts of thionyl chloride are added to a stirred mixture of 50 parts of 3,6-dichlorophthalic anhydride and 150 parts of sulfolane at 35° C., and the reaction mixture is heated to 105° C. in the course of 10 minutes and then stirred for a further 20 minutes at this temperature. Excess thionyl chloride is then stripped off in the course of 10 minutes under reduced pressure from a water pump. 30.7 parts of potassium fluoride are then added to the hot mixture, and stirring is continued for 2 hours at 220° C. The mixture is cooled, and working up is carried out as described in Example 1, but at 225° C./0.3 mbar. Subsequent azeotropic distillation with 30 parts of sulfolane gives a total of 213.5 parts of distillate. It contains 33.5 parts (79% of theory) of 3,6-difluorophthalic anhydride. A sample filtered off under suction and washed with toluene has a melting point of from 205° to 207° C. Gas chromatographic investigation shows that the filtrate contains, apart from sulfolane, only pure 3,6-difluorophthalic anhydride.

EXAMPLE 4

50 parts of phosgene are pasted into a stirred mixture of 450 parts of sulfolane and 250 parts of 4-chlorophthalic anhydride at 100° C. in the course of 40 minutes. Residual phosgene is then stripped off in the course of 10 minutes at 100° C. under reduced pressure from a water pump. 95.4 parts of potassium fluoride are then added to the hot mixture, and stirring is continued for 3½ hours at 215° C. After cooling, working up as described in Example 1 and subsequent azeotropic distillation with 126 parts of sulfolane, a total of 753.2 parts of distillate is obtained. It contains 177.2 parts (78% of theory) of 4-fluorophthalic anhydride, which is pure according to gas chromatography. A sample precipitated with water has a melting point of 78°–81° C.

We claim:

1. A process for the preparation of a fluorophthalic anhydride of the formula

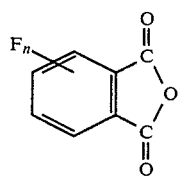

by reacting a chlorophthalic anhydride of the formula

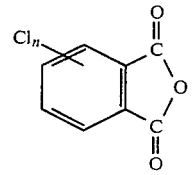

where n has the above meanings, with potassium fluoride in the presence of an aliphatic sulfone as a solvent, wherein the chlorophthalic anhydride is treated with an acid chloride of sulfurous acid or of carbonic acid in the presence of the aliphatic sulfone at as high as 150° C., and the reaction mixture is then reacted with potassium fluoride at from 150° to 250° C.

2. A process as claimed in claim 1, wherein thionyl chloride or phosgene is used as the acid chloride of sulfurous acid or of carbonic acid.

* * * * *